(12) United States Patent
Giannella

(10) Patent No.: US 7,559,911 B2
(45) Date of Patent: Jul. 14, 2009

(54) BLOOD CHAMBER FOR EXTRACORPOREAL BLOOD CIRCUITS AND A PROCESS FOR MANUFACTURING THE BLOOD CHAMBER

(75) Inventor: Carlo Giannella, Mirandola (IT)

(73) Assignee: Gambro Lundia AB (SE)

( * ) Notice: Subject to any disclaimer, the term of this patent is extended or adjusted under 35 U.S.C. 154(b) by 418 days.

(21) Appl. No.: 10/915,394

(22) Filed: Aug. 11, 2004

(65) Prior Publication Data
US 2005/0054968 A1    Mar. 10, 2005

Related U.S. Application Data

(60) Provisional application No. 60/530,512, filed on Dec. 17, 2003.

(30) Foreign Application Priority Data
Sep. 5, 2003    (IT)    .................. MO2003A0244

(51) Int. Cl.
*A61M 37/00* (2006.01)
*A61B 19/00* (2006.01)

(52) U.S. Cl. .................. 604/6.15; 604/403; 604/408

(58) Field of Classification Search .................. 604/403, 604/408, 409, 410, 6.15, 533, 535, 537; 383/210.1
See application file for complete search history.

(56) References Cited

U.S. PATENT DOCUMENTS

| | | | |
|---|---|---|---|
| 3,778,973 A | | 12/1973 | Martinez |
| 4,140,162 A | * | 2/1979 | Gajewski et al. ............ 428/35.5 |
| 4,289,337 A | * | 9/1981 | Roe .......................... 285/136.1 |
| 4,345,919 A | | 8/1982 | Wilkinson et al. |
| 4,417,753 A | * | 11/1983 | Bacehowski et al. ....... 285/21.1 |
| 4,681,606 A | | 7/1987 | Swan, Jr. et al. |
| 4,816,221 A | * | 3/1989 | Harvey et al. ................. 422/25 |
| 4,826,477 A | * | 5/1989 | Adams ....................... 604/4.01 |

(Continued)

FOREIGN PATENT DOCUMENTS

EP    0 358 963 A1    3/1990

(Continued)

OTHER PUBLICATIONS

International Search Report of International Application No. PCT/IB2004/002306.

*Primary Examiner*—Leslie R Deak
(74) *Attorney, Agent, or Firm*—Finnegan, Henderson, Farabow, Garrett & Dunner L.L.P.

(57) ABSTRACT

A blood chamber for extracorporeal blood circuits comprises a container body (2) made in a single piece by blowing of a plastic material, and has a plurality of connection ports (3, 4) for fluid communication with outside; each connection port (3, 4) comprises a tubular mouth (6) having a truncoconical internal surface (61) which is coupled in a fluid-proof coupling to a tubular first part (101) of an insert (10), made by injection molding of a plastic material. The insert (10) has a truncoconical and smooth internal surface (102) which is coupled by gluing with a solvent to an end zone of a fluid transport tube (7, 8). The coupling between the blood chamber and the fluid transport tubes is very strong and reliable. The blood chamber is part of an extracorporeal blood circuit which is operatively associated to a dialysis machine.

23 Claims, 2 Drawing Sheets

U.S. PATENT DOCUMENTS

| | | | |
|---|---|---|---|
| 5,061,365 A | 10/1991 | Utterberg | |
| 5,328,461 A | 7/1994 | Utterberg | |
| 5,330,425 A | 7/1994 | Utterberg | |
| 5,445,623 A | 8/1995 | Richmond | |
| 5,520,640 A | 5/1996 | Utterberg | |
| 5,578,070 A | 11/1996 | Utterberg | |
| 5,591,251 A | 1/1997 | Brugger | |
| 5,605,540 A | 2/1997 | Utterberg | |
| 5,637,102 A * | 6/1997 | Tolkoff et al. | 604/536 |
| 5,643,205 A | 7/1997 | Utterberg | |
| 5,674,397 A | 10/1997 | Pawlak et al. | |
| 5,769,815 A * | 6/1998 | Utterberg | 604/80 |
| 5,904,676 A | 5/1999 | Van Driel | |
| 5,980,741 A | 11/1999 | Schnell et al. | |
| 6,010,623 A | 1/2000 | Schnell et al. | |
| 6,019,824 A | 2/2000 | Schnell | |
| 6,051,134 A | 4/2000 | Schnell et al. | |
| 6,117,342 A | 9/2000 | Schnell et al. | |
| 6,165,149 A | 12/2000 | Utterberg et al. | |
| 6,171,484 B1 | 1/2001 | Schnell et al. | |
| 6,206,954 B1 | 3/2001 | Schnell et al. | |
| 6,517,508 B1 | 2/2003 | Utterberg et al. | |
| 2005/0059951 A1 * | 3/2005 | Young | 604/403 |

FOREIGN PATENT DOCUMENTS

| | | |
|---|---|---|
| EP | 0 568 275 B1 | 11/1993 |
| EP | 0 579 916 | 1/1994 |
| EP | 0 606 483 A1 | 7/1994 |
| EP | 0 800 839 A2 | 10/1997 |
| WO | WO 90/11812 | 10/1990 |
| WO | WO 98/23353 | 6/1998 |
| WO | WO03/035224 A1 | 5/2003 |

* cited by examiner

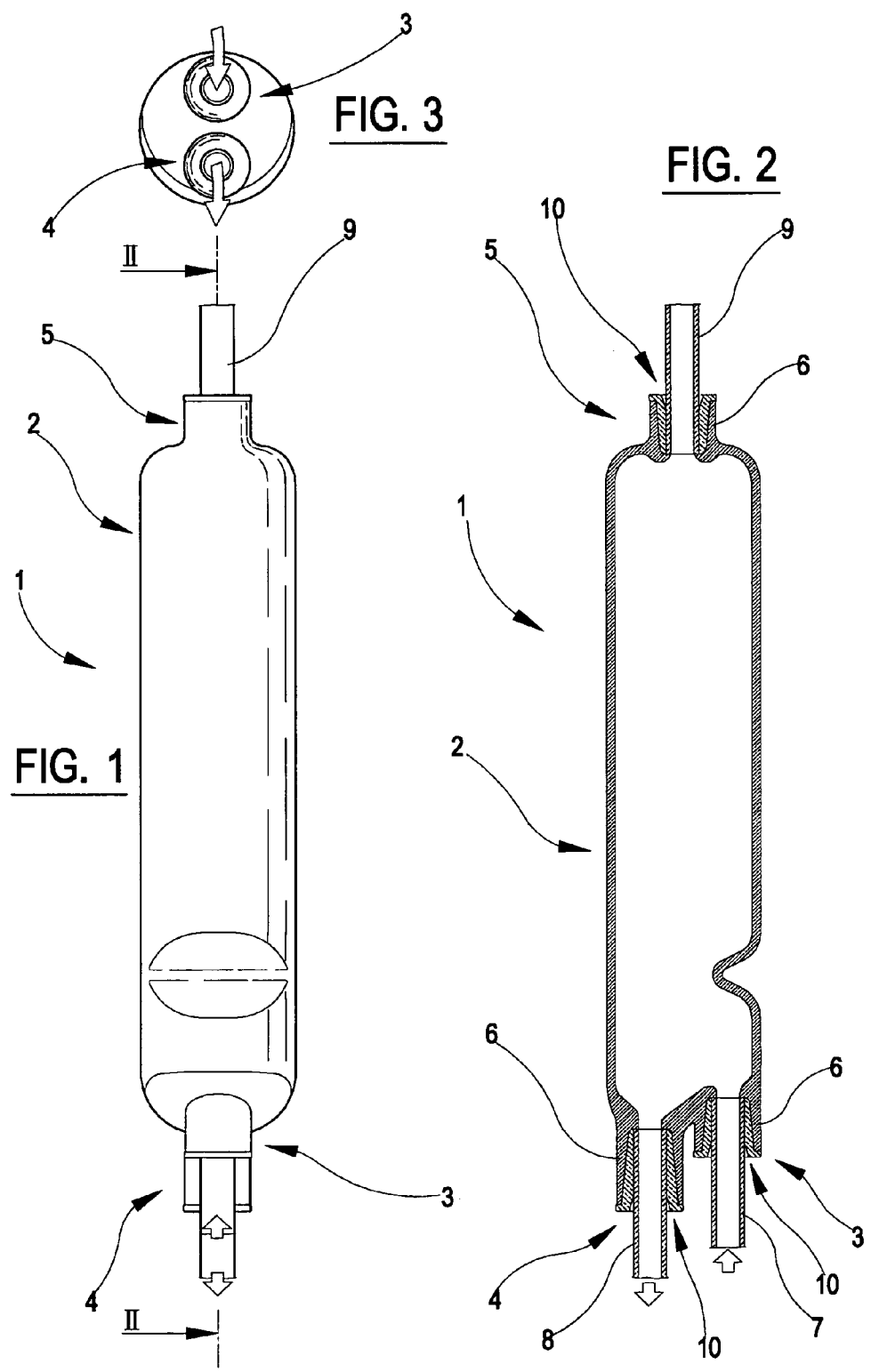

BLOOD CHAMBER FOR EXTRACORPOREAL BLOOD CIRCUITS AND A PROCESS FOR MANUFACTURING THE BLOOD CHAMBER

This application claims the priority of Italian Application No. MO2003 A 000244, filed Sep. 5, 2003, and the benefit of U.S. provisional application No. 60/530,512, filed Dec. 17, 2003.

BACKGROUND OF THE INVENTION

The invention relates to a blood chamber for extracorporeal circuits and to a process for manufacturing the blood chamber.

Specifically, though not exclusively, the invention can be usefully applied in extracorporeal circuits destined to be associated to a machine for extracorporeal blood treatment, such as for example a dialysis machine.

In particular the invention relates to a blood chamber for extracorporeal circuits made according to the preamble of the first claim.

The prior art comprises blood chambers of the above-cited type, described for example in U.S. Pat. No. 5,643,205, U.S. Pat. No. 5,605,540, U.S. Pat. No. 5,520,640, U.S. Pat. No. 5,578,070, U.S. Pat. No. 5,330,425, U.S. Pat. No. 5,328,461, U.S. Pat. No. 5,061,365, U.S. Pat. No. 4,681,606.

One of the drawbacks of blood chambers, manufactured by blowing plastic materials, of known type, is that the connection of the flexible fluid transport tubes to the access ports of the chamber can, in some cases, present imperfect fluid sealing.

This is mainly connected to the fact that the connection occurs by application, on at least one of the coupling surfaces, of a solvent which, by effect of the melting of a surface layer of material, causes reciprocal adhesion of the surfaces: a connection made in this way, in order to be effective, requires that the shape and sizes of the connected coupling surfaces be very precise. This cannot however be guaranteed in the case of an access port of a blood chamber produced by blowing of plastic material, because the shape and size of the internal surface of any access port, i.e. the surface destined to be coupled with the external surface of an end zone of a flexible tube for fluid transport, can be predeterminable only within a relatively large range of values.

SUMMARY OF THE INVENTION

Given this situation, an aim of the present invention is to provide a solution to the above-described drawback in the prior art.

A further aim of the invention is to realize a blood chamber which is constructionally simple and economical and advantageously usable in an extracorporeal blood circuit, for example a dialysis circuit.

A further aim of the invention is to provide a simple process which is also reliable and economical for realizing a blood chamber for extracorporeal circuits.

An advantage of the invention is that it provides a blood chamber which can be manufactured, at least for the most part, in a non-PVC plastic material.

A further advantage of the present invention is that it makes available a blood chamber which is couplable to one or more fluid transport tubes, in which the coupling is very tenacious and reliable, and furthermore can be obtained simply and practically.

These aims and advantages and more besides are all obtained by the invention, as it is characterised in one or more of the appended claims.

A characteristic of the invention is that the blood chamber comprises at least one tubular mouth, provided with a tubular insert which is destined to couplingly receive an end zone of a fluid transport tube.

In an embodiment of the invention, the container body is formed by blowing plastic material, while the insert is formed by injection molding of plastic material.

In a further embodiment of the invention, the insert has a lateral internal surface, for coupling with the fluid transport tube, which is smooth and truncoconical and converges towards an internal part of the chamber.

In a further embodiment of the invention, the tubular mouth and the insert have corresponding lateral surfaces, having converging diameters and being joined continuously or discontinuously towards an inside of the chamber.

In an embodiment of the invention, the insert has a flanged part which covers a front end surface off the tubular mouth.

In a further embodiment of the invention, the blood chamber is structured and dimensioned for insertion in an extracorporeal circuit.

In an embodiment of the invention, an extracorporeal circuit for dialysis comprises at least one blood chamber made according to the invention.

Further characteristics and advantages of the present invention will better emerge from the detailed description that follows, of at least one embodiment of the invention which is illustrated by way of non-limiting example in the figures of the drawings.

BRIEF DESCRIPTION OF THE DRAWINGS

A description of the invention follows, with reference to the accompanying figures of the drawings, provided as a non-limiting representation of the invention, and in which:

FIG. 1 is a view in vertical elevation of a blood chamber made according to the invention;

FIG. 2 is a section made according to line II-II of FIG. 1;

FIG. 3 is a view from below of FIG. 1;

Figure 4:
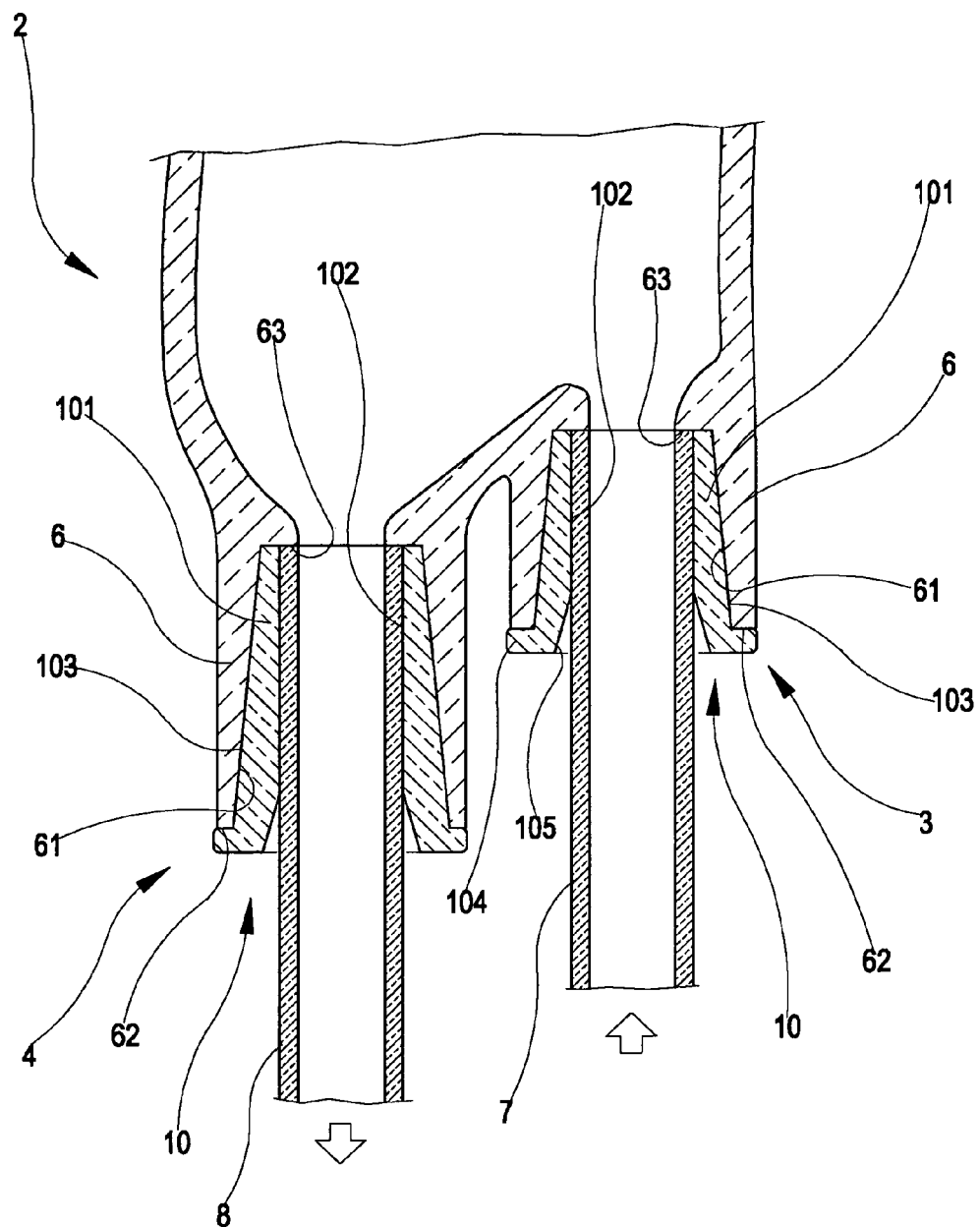
FIG. 4 is an enlarged detail of FIG. 2.

DETAILED DESCRIPTION 1 denotes in its entirety a blood chamber for extracorporeal circuits comprising a container body 2 for the blood, made in a single piece by blowing plastic material. The material the container body 2 is made of is suitable for forming by blowing. In particular, the container body 2 is made of a plastic material which is not PVC or does not contain PVC or other chlorides, for example PET.

In the specific case the blood chamber 1 is structured and sized in order to perform the function of an arterial chamber, which is to say it is destined for insertion in an arterial line (or blood removal line from a patient) of an extracorporeal circuit, such as for example a dialysis circuit, of known type and not illustrated. The arterial line, as is known, serves to remove the blood from a vascular access of a patient and transport it towards a device for blood treatment (for example a dialysis filter).

The container body 2 has, in the illustrated embodiment, an elongate shape, with an essentially cylindrical lateral wall, and has a longitudinal axis which is arranged vertically in the operative configuration (FIGS. 1 and 2). The shape of the container body 2 is of known type.

The blood chamber 1 has a plurality of connection ports for communication of fluid with the outside.

In the illustrated embodiment the connection ports comprise: a blood inlet port 3, a blood outlet port 4, a service port 5 (usable for example for pressure readings in the blood chamber, in which case a fluid transport line is inserted, which is connected to a pressure reading device).

At least a first connection port is situated in a lower zone of the container body 2. In the illustrated embodiment two lower connection ports are provided, i.e. a blood inlet port 3 and a blood outlet port 4. At least a second connection port is situated in an upper zone of the container body 2: in the illustrated embodiment an upper connection port is provided, i.e. the service port 5. The terms "lower" and "upper" are intended with reference to the operative configuration of the blood chamber 1, which in the illustrated embodiment is represented by the configuration in which the longitudinal axis of the chamber is vertical (FIGS. 1 and 2). In the illustrated embodiment, the lower ports are located on a bottom of the container body 2, and the upper port is located at a top of the container body 2.

Other embodiments of the invention are possible, not illustrated, in which the blood chamber exhibits a container body, of known type, having a shape and size which is different from those described above, or provided with access ports having a number and disposition (also of known type) different to what is described herein.

Each connection port 3, 4 and 5, comprises a tubular mouth 6, having an internal surface 61 which is destined to be coupled with an end zone of a tube 7, 8 and 9 for fluid transport. The tubes 7, 8 and 9 are, for example, flexible PVC tubes normally used for fluid transport (for example blood) in medical apparatus.

The internal surface 61 for coupling the tubular mouths 6 has an internal diameter which is smaller than an internal size of the container body 2, considered in a horizontal direction, with reference to an operative configuration of the blood chamber (the configuration is the practically vertical one shown in FIGS. 1 and 2). In the illustrated embodiment, in which the internal coupling surface 61 for coupling the tubular mouths 6 exhibits a non-constant diameter (as will be better explained herein below), the container body 2 has an internal diameter which is bigger than the biggest internal diameter of each tubular mouth 6.

Each tubular mouth 6 is made in a single piece together with the container body 2, during the same forming operation (for example by plastic material blowing).

Each tubular mouth 6 emerges from the main part of the container body 2, directed externally of the container body 2.

Each tubular mouth 6 has a vertical axis, where "vertical" is taken to mean with reference to the operative configuration of the blood chamber 1.

The internal lateral coupling surface 61 of each tubular mouth 6 has at least one first transversal section, more external (with reference to the container body 2), having a bigger diameter with respect to at least a second and more internal transversal section. In other words, the internal coupling surface 61 of each tubular mouth 6 exhibits at least one variation in diameter, discrete or continuous, which leads to a narrowing of the passage section towards the inside of the container body 2. In the illustrated embodiment, the convergence towards the inside of the container body 2 is realized with the internal coupling surface 61 of each tubular mouth 6 being essentially truncoconical in shape, as can be better seen from the enlarged view of FIG. 4.

Each tubular mouth 6 is provided with an insert 10, made of a plastic material, which has a first tubular part 101 that covers at least a part of the internal lateral coupling surface 61 of the tubular mouth 6.

The first tubular part 101 is destined to be interposed between the internal lateral coupling surface 61 of the tubular mouth 6 and the end zone of the tube 7, 8 and 9 destined for connection with the access port 3, 4 and 5.

In particular, the first tubular part 101 has an internal lateral surface 102 which is destined to receive, in a contact coupling which is fluid-proof sealed, the end zone of the tube 7, 8 and 9. The internal lateral surface 102 of the first tubular part 101 is an essentially truncoconical surface (converging towards the inside of the chamber), and is smooth and coaxial to the tubular mouth 6, and has precise predetermined dimensions so that the connection with the tube, achieved in a known way, for example by gluing with a solvent, is unmovable, reliable and resistant.

The first tubular part 101 also has an external lateral surface 103, which converges in an internal direction of the container body 2, and is truncoconical and joined to the corresponding internal lateral coupling surface 61 of the tubular mouth 6.

Each insert 10 exhibits, therefore, an internal lateral coupling surface 102 (with one of the tubes 7, 8 or 9) which is at least partially truncoconical in shape or in any case converges towards the inside of the blood chamber, and an external lateral coupling surface 103 (for coupling with the corresponding tubular mouth 6) which is at least partly truncoconical in shape, or in any case converging towards the inside of the blood chamber.

The internal lateral surface 102 of the insert 10 can have an initial part 105, for the first part of the insertion in the tube, which is truncoconical with greater convergence with respect to a more internal part of surface destined for coupling.

Each insert 10 is made of a plastic material which is formable by injection-molding, such as for example soft (plasticized) or rigid PVC. The proposed solution enables, with considerable reliability, the internal diameter of the coupling surface 102 to be obtained with precision, i.e. the precision which is necessary for realizing a coupling with the tube 7, 8 and 9, strong and resistant over time while giving an extremely reliable seal.

Each insert 10 is made in a single piece.

The plastic material the insert 10 is made of can be different from the plastic material the container body 2 is made of. In particular, the insert 10 can be made of PVC, either rigid or soft, while the container body 2, as well as the connection ports 3, 4 and 5 on the container 2, can be made in a non-PVC material which is free of chlorides (for example, PET).

Each insert 10 has a flanged second part 104 which emerges radially from an annular end of the first tubular part 101. The flanged second part 14 covers a front end surface 62 of the corresponding tubular mouth 6. The flanged second part 104 is, in certain situations, superposed and in contact with the front end surface 62 of the tubular mouth 6.

The blood chamber 1 can be manufactured by first performing the forming of the insert 10, separately from the container body 2 and then, in a second stage, applying the insert 10 on the corresponding tubular mouth 6 located on the container body 2.

The application of the insert 10 can be done by inserting the insert 10 into the tubular mouth 6 up until at least one surface of the insert 10 contacts a surface of the tubular mouth 6.

The surface of the insert 10 which contacts the mouth 6 can be, for example, the flanged second part 104 thereof, which strikes against the striking surface of the tubular mouth 6, which in the present embodiment is the front end surface 62 of the tubular mouth 6, which is arranged externally of the tubular mouth 6 with respect to the container.

The insert striker surface can also be, according to the shapes and/or sizes of the various elements involved in the coupling, the truncoconical lateral external surface 101, which on insertion strikes against the truncoconical internal lateral surface of the tubular mouth 6.

The special conformation and arrangement of the insert 10 and the tubular mouth 6 ensure that by effect of the insertion of the insert 10 in the tubular mouth 6, there is in all cases the presence of pairs of joined surfaces—a surface of the pair belonging to the insert 10 and the other surface of the pair belonging to the tubular mouth 6—in which there is reciprocal contact over a relatively large surface area. This presence of pairs of coupled surfaces in reciprocal contact is guaranteed even if the surfaces themselves are not realized with extreme precision in terms of shape and size, as for example in a case in which the tubular mouth 6 is made by plastic material blowing in a single piece with the whole container body 2. In other words, even if the tubular mouth 6 were made by a blowing technique, in a single body with the container 2, with relatively poor precision, the coupling between the insert 10 and the tubular mouth 6 would be safe, strong and resistant in any case. Thanks to the presence of relatively large areas of coupling surfaces, a coupling can be guaranteed between the insert 10 and the tubular mouth 6 which is especially effective and reliable. This coupling can be, for example, obtained by gluing. In more detail the coupling can be glued using solvent, for example a suitable solvent for PVC, applied on the external surface of the insert 10.

The coupling between the tube and the insert is realized between contact surfaces that can require high constructional precision. This precision is guaranteed, in the case of the insert 10, by the fact that it can be made separately, or at a different time, with respect to the container body 2, with processes and know-how which are specific and suitable for realizing a tubular insert 10, which is relatively much smaller than the container body 2, with shapes and sizes of especially accurate tolerances and precision.

In particular, the insert can be made by injection molding of plastic material, rather than by plastic material blowing as in the case of the container body 2.

As mentioned, the blood chamber described herein is the arterial chamber of an extracorporeal blood circuit for dialysis. The circuit comprises a flexible tubing circuit, at least a part of which is fluidly and solidly connected to the connection ports of the blood chamber.

Each tube is associated to a corresponding connection port having an end zone coupled and fluid-sealed, with an unmovable coupling (for example by gluing using a solvent) with the internal surface of the first tubular part of the relative insert.

The blood chamber is manufactured using a process comprising a stage of realizing, by plastic-material blowing, a container body 2 having a plurality of connection ports for fluid communication with outside the body. Each connection port comprises a tubular mouth made in a single piece with the container body; each tubular mouth has an internal transversal size which is smaller than an internal transversal size of the container body 2.

The process also includes a subsequent stage of application, on each tubular mouth, of an insert made of plastic material having a tubular part which, by effect of the application, covers a part of an internal surface of the tubular mouth.

Each insert is applied to the corresponding tubular mouth by a fluid-sealed coupling.

In a first embodiment of the process, already cited and described herein above, an insert is first made by plastic-material injection molding, and thereafter the insert is applied, for example by gluing using a solvent. In a second embodiment of the process, the application of the insert comprises an injection molding of plastic material directly on the tubular body. In this case the coupling between insert and tubular mouth is realized by friction grip.

The extracorporeal circuit is manufactured by application of an end zone of a flexible fluid transport tube internally of the tubular part of each insert.

In this description reference has been made to a specific application relating to an arterial chamber for dialysis; it is however possible to apply the invention to other purposes, such as for example a chamber structured and sized to carry out the function of a venous chamber, destined for insertion in a venous line of an extracorporeal circuit.

The invention claimed is:

1. A blood chamber comprising a container body for blood having a plurality of connection ports for fluid communication with outside the container body, each of the plurality of connection ports comprising a tubular mouth configured to be coupled to an end zone of a tube, wherein:
   each tubular mouth is made in a single piece with the container body;
   at least one of the tubular mouths is provided with an insert having a surface configured to receive in a fluid-proof sealed coupling the end zone of the tube; and
   the insert has at least one first tubular part covering at least a part of an internal surface of the tubular mouth, said at least one first tubular part being configured to be interposed between the internal surface of the tubular mouth and the end zone of the tube, wherein said tubular mouth has an internal surface with at least a first transversal section and at least a second transversal section, the first transversal section being, with reference to the container body. more external than the second transversal section, the more external first transversal section having a larger diameter than a diameter of the internal second transversal section.

2. The chamber of claim 1, wherein said insert surface, configured to receive, in a fluid-proof sealed coupling contact, the end zone of the tube, is an internal surface of said first tubular part.

3. The chamber of claim 1, wherein said internal surface of the tubular mouth has an internal diameter which is smaller than an internal diameter of said container body, the internal diameter of the container body being in a horizontal direction with reference to a vertical operative configuration of the blood chamber.

4. The chamber of claim 1, wherein the container body is made in a single piece.

5. The chamber of claim 1, wherein the container body is made of a plastic material which is formable by blow molding.

6. The chamber of claim 1, wherein each tubular mouth emerges from the container body in an external direction.

7. The chamber of claim 1, wherein the plurality of connection ports comprises at least a first connection port located in a lower zone of the container body, and at least a second connection port located in an upper zone of the container body, where lower and upper refer to a vertical operative configuration of the blood chamber, each of the first connection port and the second connection port comprising a tubular mouth provided with the insert.

8. The chamber of claim 1, wherein the tubular mouth, provided with the insert, has a vertical axis, where vertical refers to a vertical operative configuration of the blood chamber.

9. The chamber of claim 1, wherein the insert is made of a plastic material.

10. The chamber of claim 9, wherein the plastic material of the insert is a material which is formable by injection molding.

11. The chamber of claim 1, wherein said insert surface, which is configured to receive, in a fluid-proof sealed coupling, the end zone of the tube, is a smooth surface.

12. The chamber of claim 1, wherein the insert is made in a single piece.

13. The chamber of claim 1, wherein the tubular mouth has an internal surface which converges towards an inside of the container body, said internal surface being joined to an external surface of the insert.

14. The chamber of claim 1, wherein said insert has a tubular part and a flanged part, said flanged part emerging radially from the tubular part and covering a front-end surface of a corresponding tubular mouth.

15. The chamber of claim 14, wherein the flanged part is superposed on and in contact with said front-end surface of the tubular mouth.

16. The chamber of claim 1, wherein said container body is made of a plastic material which is not PVC or which is free of chlorides.

17. The chamber of claim 1, wherein the chamber is an arterial chamber which is structured and sized for insertion in an arterial line of an extracorporeal circuit.

18. The chamber of claim 1, wherein the chamber is a venous chamber which is structured and sized for insertion in a venous line of an extracorporeal circuit.

19. The chamber of claim 1, wherein said insert is made of a first plastic material, said container body being made of a second plastic material which is different than the first plastic material.

20. An extracorporeal circuit comprising a circuit of tubes, and at least one blood chamber provided with a plurality of connection ports, at least one of the tubes being connected to each of the connection ports, wherein the at least one blood chamber is made according to claim 1.

21. The circuit of claim 20, wherein at least one of said tubes connected to the connection port has an end zone which is fluid-sealed and unmovably coupled with said insert surface of the relative connection port.

22. A blood chamber comprising a container body for blood having a plurality of connection ports for fluid communication with outside the container body, each of the plurality of connection ports comprising a tubular mouth configured to be coupled to an end zone of a tube, wherein:
  each tubular mouth is made in a single piece with the container body; and
  at least one of the tubular mouths having an insert having a surface configured to receive the end zone of the tube in a fluid-proof sealed coupling, said insert having at least a first tubular part covering at least a part of an internal surface of the tubular mouth, said at least one first tubular part being configured to be interposed between the internal surface of the tubular mouth and then end zone of the tube, wherein the tubular mouth has an internal surface that converges toward an inside of the container body, said internal surface being joined to an external surface of the insert.

23. A blood chamber according to claim 1, wherein the first tubular part of the insert has an external lateral coupling surface at least part of which converges toward the inside of the blood chamber.

* * * * *